(12) United States Patent
Tolbert et al.

(10) Patent No.: US 11,406,252 B2
(45) Date of Patent: Aug. 9, 2022

(54) PORTABLE AND STERILIZABLE LIGHT SOURCE

(71) Applicant: Sunoptic Technologies LLC, Jacksonville, FL (US)

(72) Inventors: Joshua Tolbert, Jacksonville, FL (US); Frank Robson, Middleburg, FL (US); Brandon Closson, St. Johns, FL (US)

(73) Assignee: Sunoptic Technologies LLC, Jacksonville, FL (US)

( * ) Notice: Subject to any disclaimer, the term of this patent is extended or adjusted under 35 U.S.C. 154(b) by 146 days.

(21) Appl. No.: 16/817,782

(22) Filed: Mar. 13, 2020

(65) Prior Publication Data

US 2020/0288956 A1 Sep. 17, 2020

Related U.S. Application Data

(60) Provisional application No. 62/818,396, filed on Mar. 14, 2019.

(51) Int. Cl.
| | |
|---|---|
| *A61B 1/06* | (2006.01) |
| *A61L 2/14* | (2006.01) |
| *A61L 2/18* | (2006.01) |
| *A61B 1/00* | (2006.01) |
| *F21L 4/08* | (2006.01) |
| *F21V 23/04* | (2006.01) |
| *F21V 31/00* | (2006.01) |

(52) U.S. Cl.
CPC ........ *A61B 1/0684* (2013.01); *A61B 1/00137* (2013.01); *A61L 2/14* (2013.01); *A61L 2/186* (2013.01); *F21L 4/08* (2013.01); *F21V 23/0421* (2013.01); *F21V 31/005* (2013.01)

(58) Field of Classification Search
CPC ............ A61B 1/00032; A61B 1/00137; A61B 1/0669; A61B 1/0684; A61L 2/14; A61L 2/186; A61L 2/208; A61L 2202/24; F21L 4/08; F21V 23/0421; F21V 31/005
See application file for complete search history.

(56) References Cited

U.S. PATENT DOCUMENTS

| | | | |
|---|---|---|---|
| 6,428,180 B1 | 8/2002 | Karrum et al. | |
| RE38,014 E * | 3/2003 | Bieberstein | ......... F21V 23/0421 200/60 |
| 6,591,049 B2 | 7/2003 | Williams et al. | |
| 6,595,676 B2 | 7/2003 | Starry | |
| 7,281,815 B1 * | 10/2007 | Gustafson | ........... F21V 23/0421 362/802 |
| 7,631,981 B2 | 12/2009 | Miller et al. | |
| 7,758,203 B2 | 7/2010 | McMahon et al. | |

(Continued)

*Primary Examiner* — Zheng Song
(74) *Attorney, Agent, or Firm* — Howson & Howson LLP

(57) ABSTRACT

A portable, sterilizable light source unit for being coupled to an instrument is provided. The unit includes a sealed housing having an anodized coating and a port for receiving an end tip of a light guide of a separate instrument, a light source mounted within the sealed housing for directing light through the port, a battery mounted within the housing for powering the light source, a switch assembly mounted on the housing for controlling light output of the light source, and an O-ring in a compressed condition between the switch assembly and the housing providing a fluid-tight seal therebetween that prevents liquid intrusion into the housing during an immersion sterilization process.

13 Claims, 7 Drawing Sheets

(56) References Cited

U.S. PATENT DOCUMENTS

| | | | |
|---|---|---|---|
| 7,802,898 B1* | 9/2010 | Gregory | G02F 1/133308 |
| | | | 362/205 |
| 8,469,540 B1* | 6/2013 | Gregory | F21V 23/0421 |
| | | | 362/205 |
| 8,905,573 B2 | 12/2014 | Sharrah et al. | |
| 10,401,001 B2 | 9/2019 | Kennedy et al. | |
| 2002/0109987 A1* | 8/2002 | Lai | F21L 4/00 |
| | | | 362/206 |
| 2007/0019398 A1* | 1/2007 | Chen | F16M 13/04 |
| | | | 362/102 |
| 2007/0247867 A1 | 10/2007 | Hunter et al. | |
| 2009/0326329 A1* | 12/2009 | Yamane | A61B 1/00032 |
| | | | 600/178 |
| 2010/0219775 A1* | 9/2010 | Maglica | F21L 4/045 |
| | | | 315/362 |
| 2012/0224358 A1* | 9/2012 | Noble | F21S 10/00 |
| | | | 362/158 |
| 2017/0225186 A1* | 8/2017 | Ferguson | B05B 1/18 |
| 2019/0338926 A1 | 11/2019 | Kennedy et al. | |

\* cited by examiner

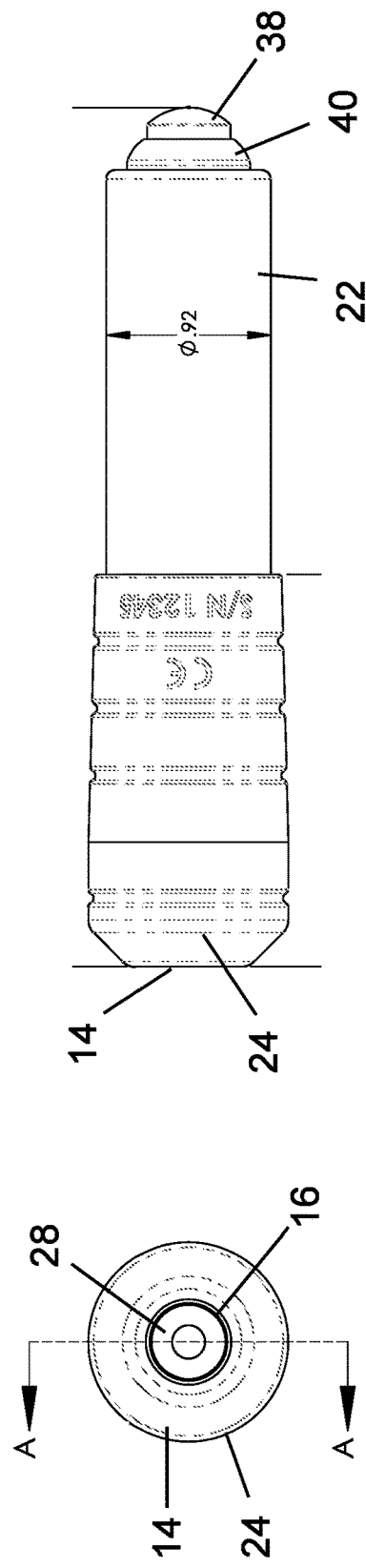
FIG 2.
FIG. 3
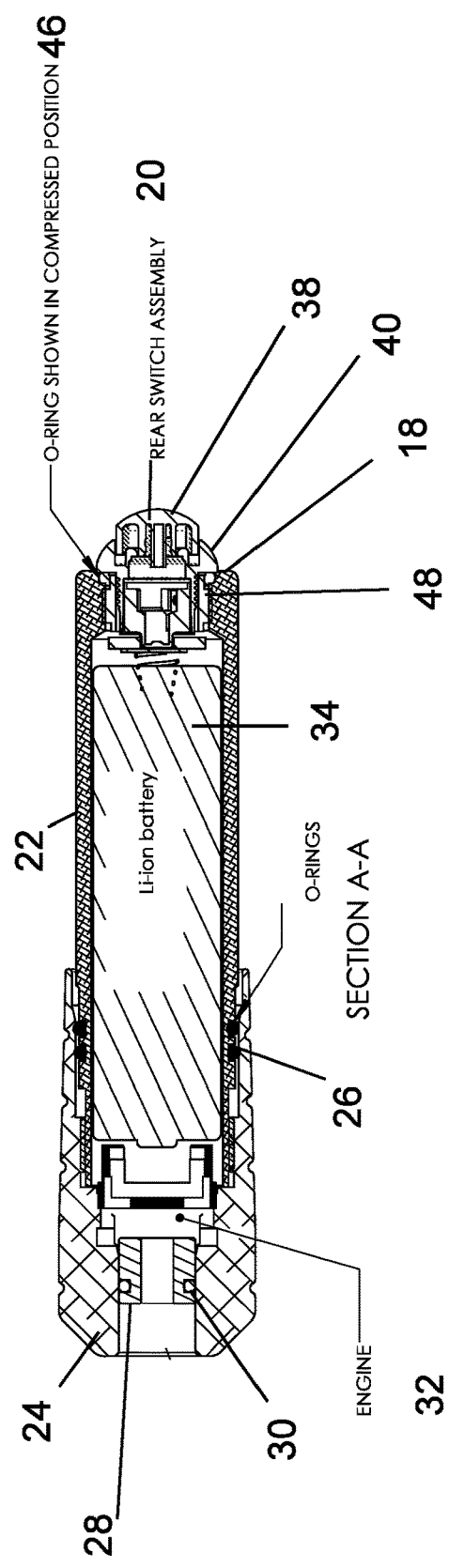
FIG. 4

US 11,406,252 B2

PORTABLE AND STERILIZABLE LIGHT SOURCE

CROSS REFERENCE TO RELATED APPLICATIONS

This application claims the benefit under 35 USC § 119(e) of U.S. Provisional Patent Application No. 62/818,396 filed Mar. 14, 2019.

BACKGROUND

The present invention relates to a light source for instruments used to illuminate a surface or cavity, and more particularly, the present invention relates to a compact, portable, light source for use with rigid or flexible endoscopes, lighted retractors, and like instruments having an integral light post to which the portable light source is connected and by which the portable light source is carried by the instrument.

By way of example, endoscopes, lighted retractors, and like instruments may be used in a hospital, health care facility, or the like, for instance, to illuminate a cavity or surface of a patient. Such instruments are typically attached to a stationary light source unit that remains in one location during use or is fastened to a rolling cart or the like and that transmits light to the instrument via a fiber optic cable that tethers the instrument to the stationary light source unit. This conventional arrangement can be inconvenient and cumbersome during use. For instance, this arrangement necessarily requires the operator to manage a cumbersome light source cart within limited available space and relatively heavy and cumbersome fiber optic cables.

SUMMARY

According to an embodiment, a portable, sterilizable light source unit adapted for being coupled to an instrument is provided. The unit includes a sealed housing having an anodized coating and a port for receiving an end tip of a light guide of a separate instrument, a light source mounted within the sealed housing for directing light through the port, a battery mounted within the housing for powering the light source, a switch assembly mounted on the housing for controlling light output of the light source, and an O-ring in a compressed condition between the switch assembly and the housing providing a fluid-tight seal therebetween that prevents liquid intrusion into the housing during an immersion sterilization process.

BRIEF DESCRIPTION OF THE DRAWINGS

The features and advantages of the present invention should become apparent from the following description when taken in conjunction with the accompanying drawings, in which:

FIG. 2 is a side elevational view of the portable light source unit of FIG. 1;

FIG. 3 is a plan view of a front end of the portable light source unit of FIG. 1;

FIG. 4 is a cross-sectional view of the portable light source unit along plane A-A of FIG. 3;

DETAILED DESCRIPTION

Figure 1:
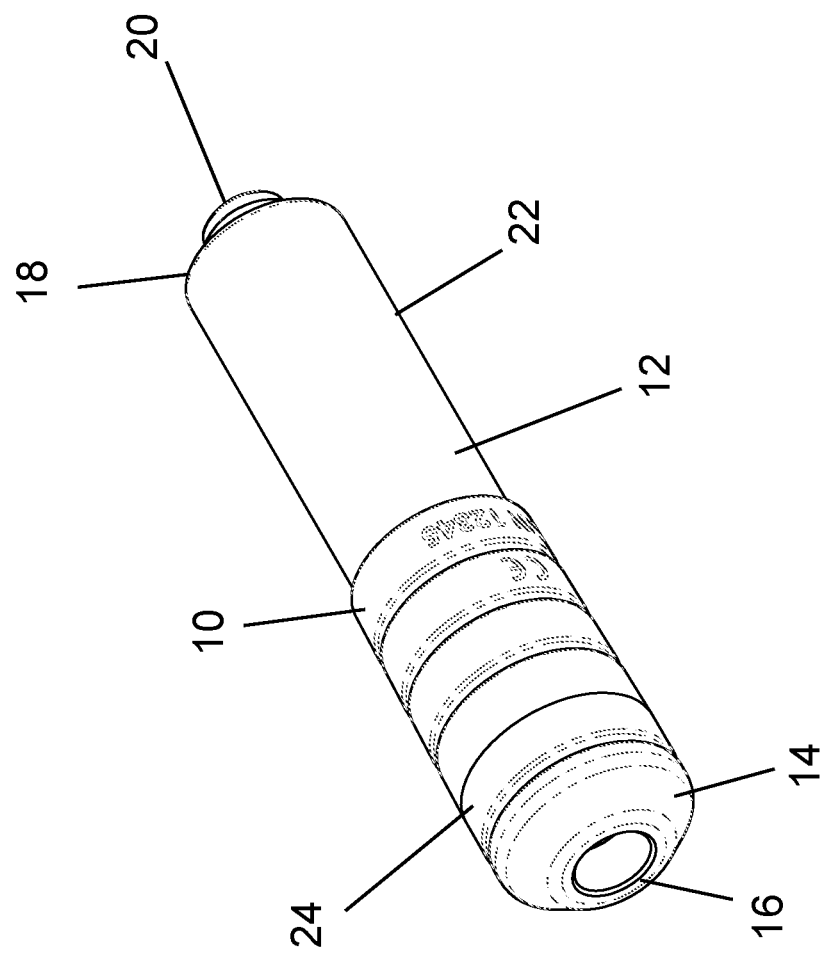
FIG. 1 is a perspective view of a portable light source unit according to an embodiment.

According to an embodiment, a compact, portable, lightweight light source unit is provided that is adapted to be readily coupled to, and decoupled from, an end tip of a light post or guide of an endoscope, lighted retractor, or like medical or non-medical instrument. The portable light source unit may be used to replace the conventional stationary light source and cable system described above. Thus, the light source unit couples directly to the instrument and is supported and carried thereby without the need for carts, outer support components, cables, tethers, fiber optic cables, or the like. The light source unit may be packaged and provided to an end user in a sterile or non-sterile condition.

According to an embodiment, the portable light source unit is submersible, for instance, for sterilization and disinfection purposes. For example, the light source unit may be sterilizable with low-temperature, hydrogen peroxide gas plasma technology, such as via STERRAD™ sterilization techniques. In addition, the exterior surface of the portable light source unit may include an anodized coating for superior color durability despite being repeatedly subjected to the above referenced sterilization process.

According to an embodiment the portable light source unit may contain a light emitting diode (LED) that generates brilliant white light, for instance, of a color temperature of 5000° K nominal. Of course, the light source could produce visible light of a different color or color temperature or other types of electromagnetic radiation and could use other than a LED to produce the light or other radiation.

According to an embodiment, the portable light source unit may provide a switch which enables variable light output. For instance, the switch may enable the light source to be turned on and off and/or may be permit a different amount of light to be output. For example, the switch may be configured to enable the light output by the LED to be at a level of 100% of maximum brightness output of the LED, or to set the light output at 60% of maximum brightness output, or to set the light output at 25% of maximum brightness output. Of course, the variable amount of light output could include other brightness levels.

According to an embodiment, the portable light source is battery operated with a rechargeable battery contained therein. For instance, the portable light source may contain a lithium-ion battery able to provide about 2.5 hours or more of operation between charges, and the light source may be provided with a set of two rechargeable batteries and an AC battery charger.

Although the portable light source unit according to an embodiment may be provided in various sizes and of various weights, one contemplated embodiment disclosed solely for purpose of example, and not by way of limitation, has the following dimension and weight characteristics: 5.1 inches (13 cm) in total length; 1.12 inches (2.8 cm) in maximum diameter; and 5.1 oz. (145 g) in weight including battery.

An example of a portable light source unit 10 according to an embodiment is shown in FIG. 1 having a generally elongate body 12 provided with a black anodized coating, a front end 14 having a light port or socket 16 for receiving a light post of an instrument (not shown) and for being carried thereby on the instrument, and a rear end 18 provided with a rear switch assembly 20 for turning the light source on and off and/or for toggling to a different light output setting (i.e., high: (100%) maximum brightness output; Medium: 60% of maximum brightness output; and Low: 25% of maximum brightness output; and Off: (0%)).

As best shown in FIG. 4, the body 12 of the portable light source 10 includes a relatively cylindrical rear body section 22 and a front heat-dissipating cap 24 with a set of O-rings 26 extending therebetween to provide a leak-free connection between the rear body section 22 and the front cap 24. The front cap 24 provides the light port 16 and may include a fiber optic holder 28 sized for connection to a fiber optic bundle (not shown). The fiber optic holder 28 is designed to channel light from the LED into a fiber optic bundle (not shown) that is the same size as the cable to which it is being attached. The fiber optic holder 28 includes an O-ring 30 providing a fluid-tight seal between the fiber optic holder 28 and the wall defining the port 16.

A light engine 32 is located within the body 12 adjacent the light port 16 to transmit light through the light port 16. The light engine 32 may include a light emitting diode (LED) or the like and corresponding electronic converter board and may be powered internally by a battery 34 located within the rear body section 22 directly behind the light engine 32. The rear switch assembly 20 may be used to control operation of the LED as discussed above and may be located directly behind the battery 34 and extend through a rear of the rear body section 22. Thus, the light port 16 is located at one end of the body 12 and the rear switch assembly 20 is located at an opposite end.

Figure 5:
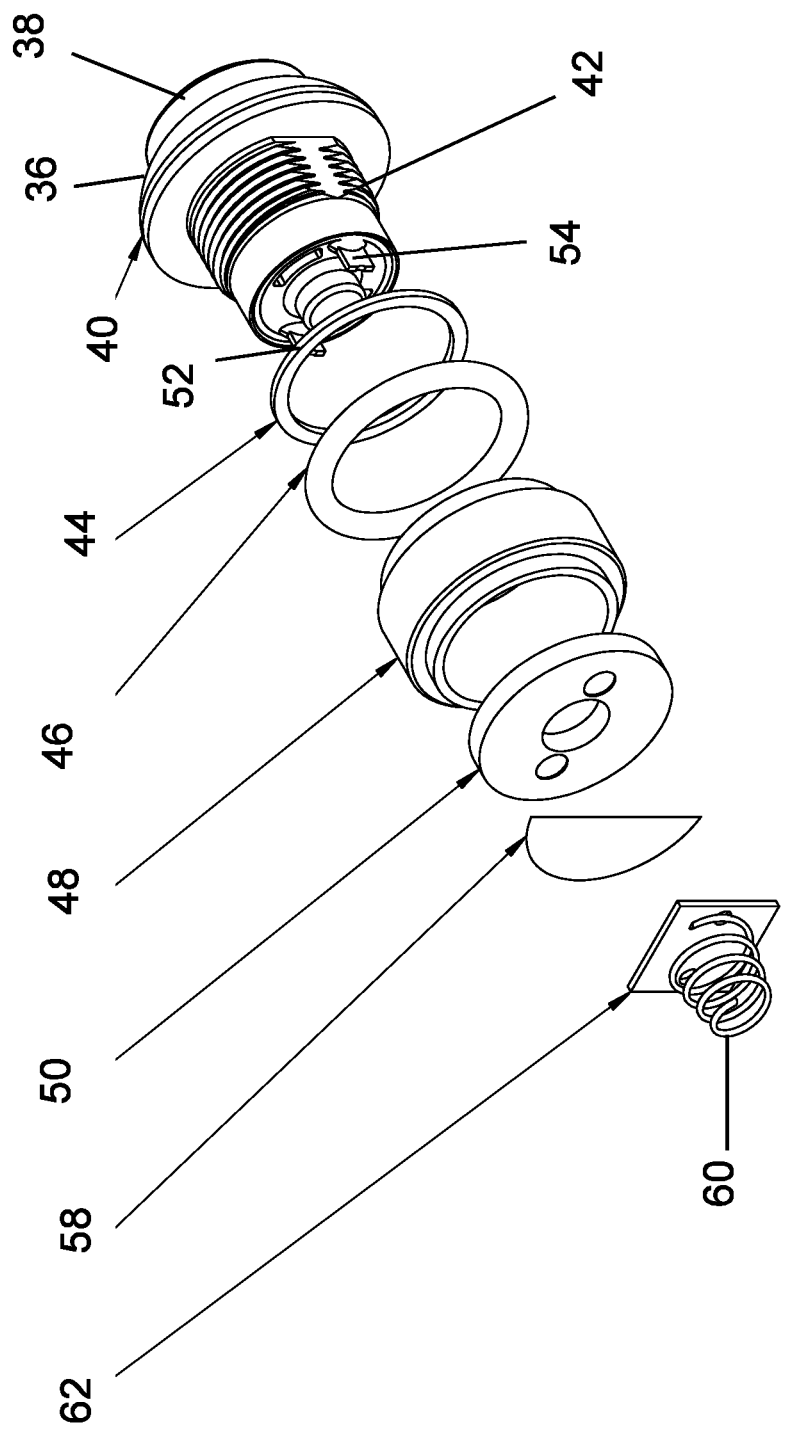
FIG. 5 is an exploded perspective view of a rear switch assembly of the portable light source unit of FIG. 1.
Figure 6:
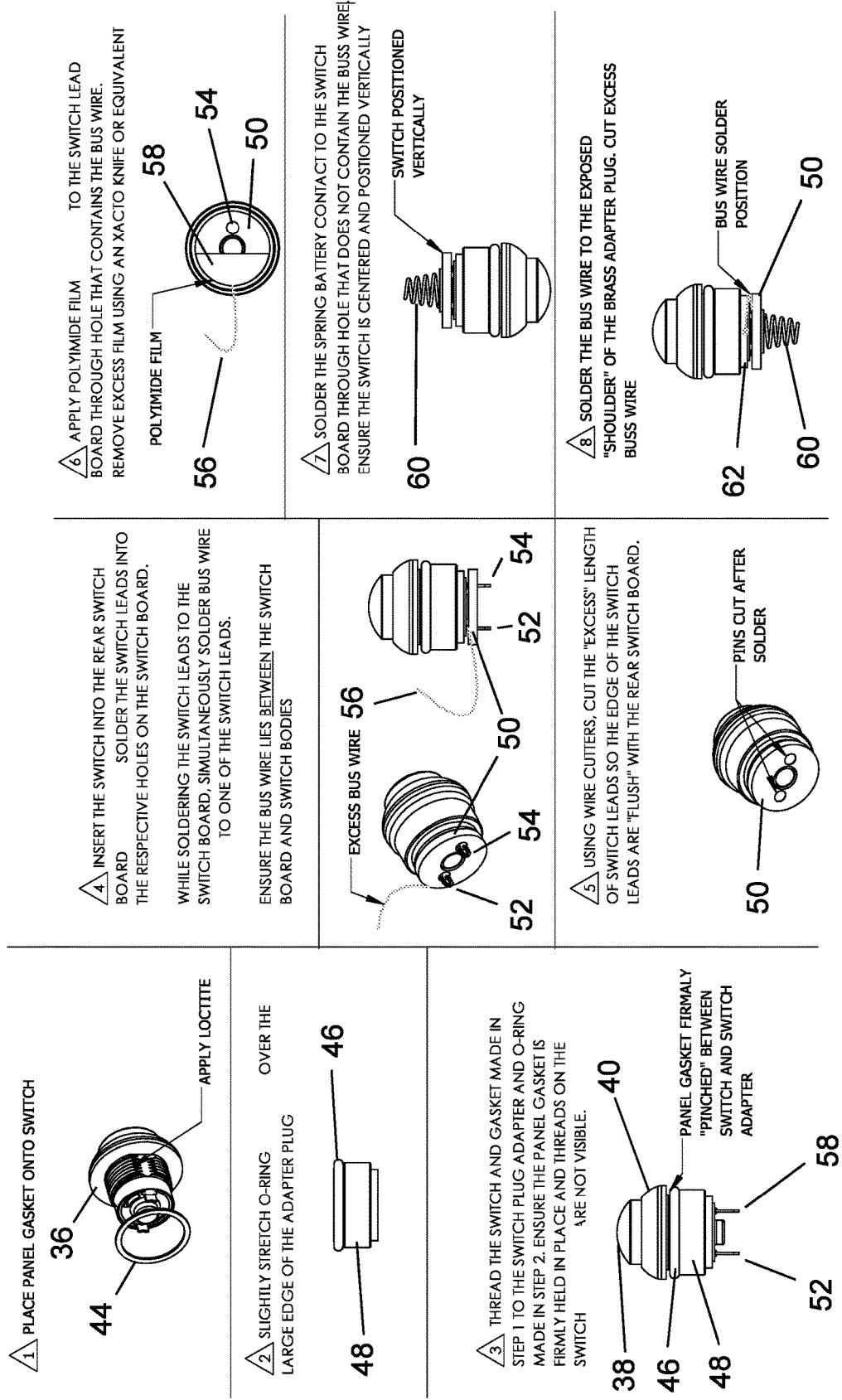
FIG. 6 is a diagram illustrating process steps for assembling the rear switch assembly of FIG. 5 according to an embodiment.
Figure 7:
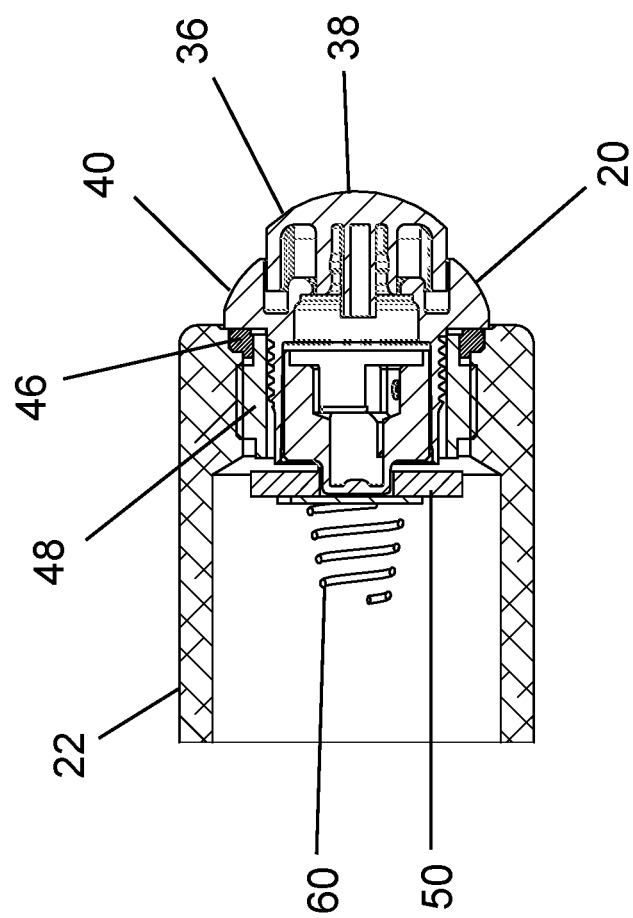
FIG. 7 is a magnified cross-sectional view of the rear switch assembly of FIG. 5 as connected to a rear of the portable light source unit of FIG. 1.

An example of the rear switch assembly 20 according to an embodiment is best shown in FIGS. 5-7. The switch assembly 20 includes a switch 36 that provides a push button 38 or like activating mechanism permitting the LED to be turned on, turned off, or dimmed and/or brightened by depressing the push button. An enlarged head 40 of the switch 36 provides a housing for the push button 38 and is exposed on the rear end 18 of the body 12 of the portable light source unit 10. An opposite end 42 of the switch 36 extends within the rear body section 22 of the portable light source 10 and an annular panel gasket 44 is applied thereto with an adhesive or the like. An O-ring 46, such as an O-ring made of a synthetic rubber, elastomer, or fluoropolymer elastomer, is then applied to a threaded switch plug adaptor 48 which is then threaded onto the end 42 of the switch 36. A rear switch circuit board 50 having a pair of openings is then applied to the plug adaptor 48 and a pair of leads, 52 and 54, of the switch 36 are soldered to the circuit board 50 at the openings. See FIG. 6. A bus wire 56 is soldered to one of the leads (i.e., lead 52 in FIG. 6) and is extended between the plug adaptor 48 and the switch circuit board 50 (see FIG. 6). Any excess length of the leads, 52 and 54, are cut with a wire cutter so that the exposed edge of the leads, 52 and 54, are flush with the surface of the rear switch circuit board 50. Thereafter, a polyimide film or tape 58 is applied over the lead to which the bus wire 56 is connected (i.e., lead 52 in FIG. 6), and a spring battery contact (i.e., a negative battery contact) 60 is soldered to the exposed lead 54 (i.e., the lead that does not connect to the bus wire 56). Finally, the bus wire 56 is soldered to the brass shoulder 62 of the plug adaptor 48.

The rear switch assembly 20, as assembled and described above, is then mounted within an opening in the rear body section 22 in the rear end 18 of the portable light source 10 such that the O-ring 46 provides a leak-free seal between the rear body section 22 and the rear switch assembly 20. See FIG. 7 which shows the O-ring 46 in a compressed condition sealing any space between the head 40 of the switch 36, the plug adapter 48 of the rear switch assembly 20, and the rear body section 22 surrounding the plug adaptor 48.

Figure 8:
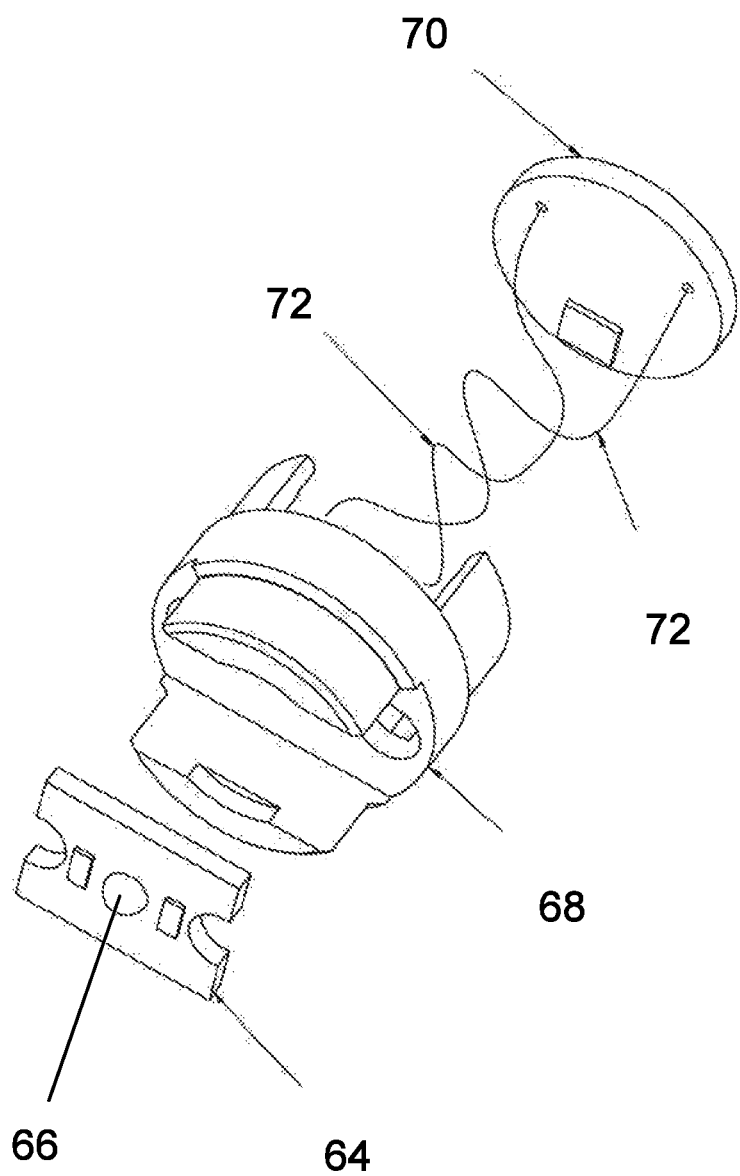
FIG. 8 is an exploded perspective view of an LED and converter board assembly within the portable light source unit of FIG. 1.

An embodiment of the light engine 32 of the portable light source is shown in greater detail in FIG. 8. The light engine 32 includes a LED printed circuit board 64 on which an LED 66 is located. The LED circuit board 64 is mounted on one side of a light engine support body 68, and a LED driver board 70 is mounted on an opposite side of the support body 68. The LED circuit board 64 and driver board 70 are interconnected with wires 72 extending through the support body 68.

Figure 9:
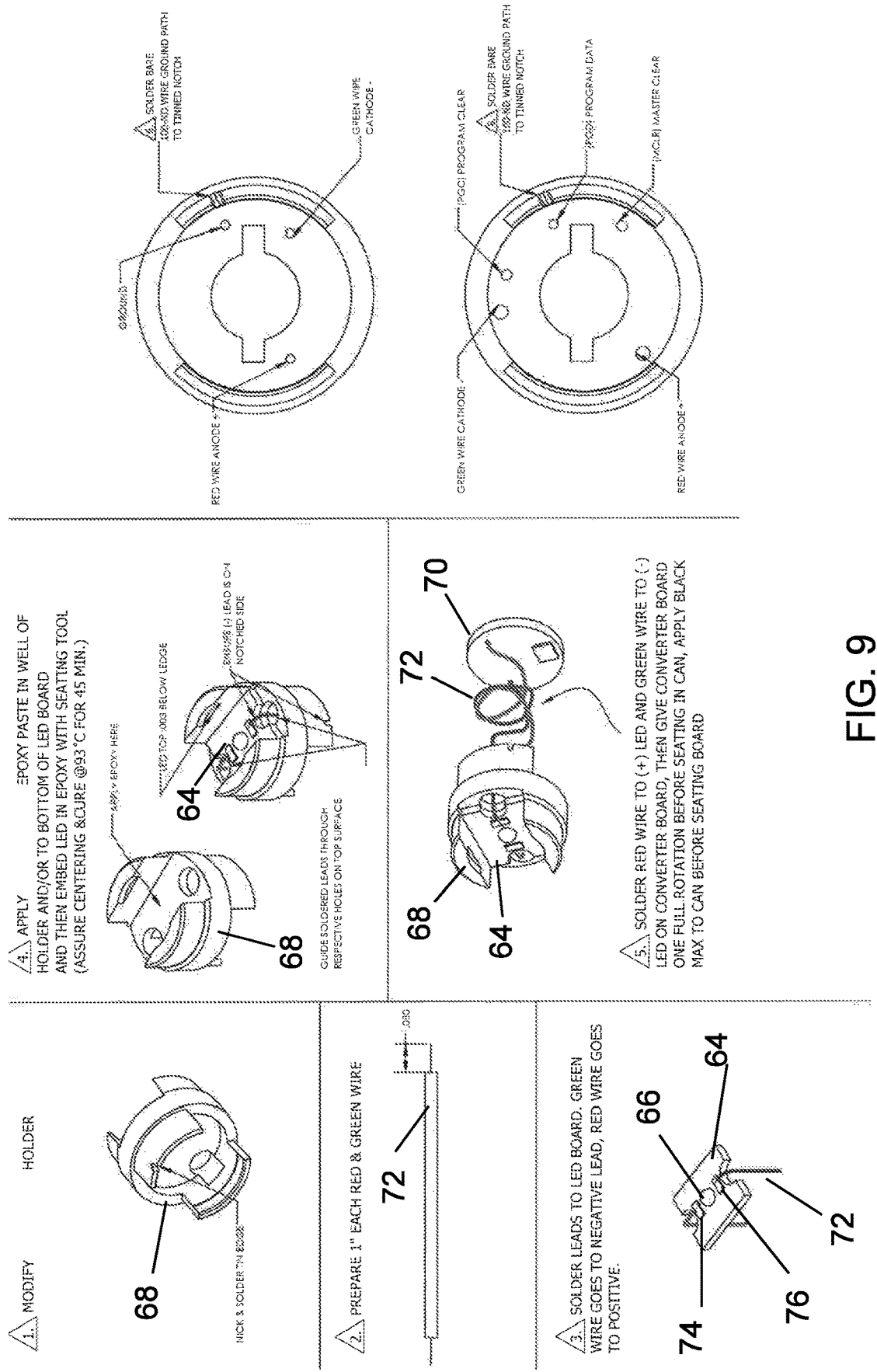
FIG. 9 is a diagram illustrating process steps for assembling the LED and converter board assembly of FIG. 8 according to an embodiment.

During assembly of the light engine 32 as shown in FIG. 9, the two wires 72 are soldered to leads, 74 and 76, of the LED circuit board 64, and the LED circuit board 64 is secured to the support body 68 with an adhesive or epoxy paste or the like. The wires 72 are fed through passages extending through the support body 68 and are soldered to the driver board 70. The driver board 70 is rotated one full turn and then secured to the support body opposite the LED circuit board 64.

Accordingly, when the portable light source 10 is assembled, the LED circuit board 64 and thus LED 66 is electrically connected to a positive battery contact of the battery 34 via the driver board 70, and the rear switch assembly 20 is electrically connected to a negative battery contact of the battery 34 via the spring battery contact 60. In addition, as stated above, when the portable light source 10 is completely assembled, the various O-rings and components permit the anodized coated body 12 to be submersible in a liquid or other fluid for being repeatedly sterilized and/or disinfected after each use of the portable light source 10 and reused.

Various modifications can be made to the embodiments of the portable light source unit such as the type of light or electromagnetic radiation emitted by the LED, the activation method, the type and size of the battery or batteries, and the shape of the port used to couple to a light post or guide of a medical or non-medical instrument. The light source unit may contain multiple or larger batteries that may provide higher or any desired level of milliampere hour (mAh) energy charge.

While a preferred portable light source unit capable of being removably coupled to an instrument has been described in detail, various modifications, alternations, and changes may be made without departing from the spirit and scope of the portable light source unit and instrument according to the present invention as defined in the appended claims.

The invention claimed is:
1. A portable, sterilizable light source unit, comprising:
   a sealed housing having a port for receiving an end tip of a light guide of a separate instrument;
   a light source mounted within said sealed housing for directing light through said port;
   a battery mounted within said housing for powering said light source;

a switch assembly mounted on said housing for controlling light output of said light source; and an O-ring in a compressed condition between said switch assembly and said housing providing a fluid-tight seal therebetween that prevents liquid intrusion into said housing during an immersion sterilization process;

wherein said housing has an anodized coating;

wherein said switch assembly includes a switch having a push button located on an exterior of said housing, said switch having an enlarged head in which said push button is mounted;

wherein said switch assembly includes a plug adapter extending within said housing and about said switch such that said plug adapter secures said switch assembly to said housing such that said O-ring is compressed between said enlarged head, said plug adapter, and said housing; and wherein said switch assembly includes a switch circuit board soldered to leads of said switch, wherein one of said leads is connected to said plug adapter via a bus wire and another of said leads is connected to a spring negative battery contact which is in contact with a negative terminal of the battery.

2. The portable, sterilizable light source unit according to claim 1, wherein said switch assembly is configured to dim or brighten light output by said light source at different light output levels.

3. The portable, sterilizable light source unit according to claim 2, wherein said housing is sterilizable with low-temperature, hydrogen peroxide gas plasma technology.

4. The portable, sterilizable light source unit according to claim 3, wherein said O-ring is made of a fluoropolymer elastomer.

5. The portable, sterilizable light source unit according to claim 1, wherein the light source is a light emitting diode (LED).

6. The portable, sterilizable light source unit according to claim 5, wherein the LED is located on a printed circuit board mounted on a support and facing said port to emit light into said port.

7. The portable, sterilizable light source unit according to claim 6, wherein a driver circuit for the LED is mounted on an opposite side of said support and is in electrical contact with the printed circuit board on which the LED is mounted and a positive terminal of said battery.

8. The portable, sterilizable light source unit according to claim 1, wherein said housing includes a cylindrical rear section to which said switch assembly is mounted and said battery is contained and a front heat-dissipating cap through which said port is defined.

9. The portable, sterilizable light source unit according to claim 8, further comprising at least one O-ring located between said front heat-dissipating cap and said rear section of said housing providing a fluid-tight seal therebetween.

10. The portable, sterilizable light source unit according to claim 1, wherein said housing is elongate having said port at one end and said switch assembly at an opposite end.

11. The portable, sterilizable light source unit according to claim 1, wherein said switch assembly includes a polyimide film located between said lead of said switch connected to said bus wire and said spring negative battery contact.

12. The portable, sterilizable light source unit according to claim 1, wherein the battery is rechargeable.

13. The portable, sterilizable light source unit according to claim 1, further comprising a fiber optic holder located within said port and an O-ring providing a fluid-tight seal between walls forming said port and said fiber optic holder.

* * * * *